United States Patent
Talwar et al.

(10) Patent No.: US 6,261,601 B1
(45) Date of Patent: Jul. 17, 2001

(54) ORALLY ADMINISTERED CONTROLLED DRUG DELIVERY SYSTEM PROVIDING TEMPORAL AND SPATIAL CONTROL

(75) Inventors: Naresh Talwar, New Delhi; Himadri Sen, Haryana, both of (IN); John N. Staniforth, Bath (GB)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/152,932

(22) Filed: Sep. 14, 1998

(30) Foreign Application Priority Data

Sep. 19, 1997 (IN) .............................................. 2660/DEL/97

(51) Int. Cl.[7] .............................. A61K 9/46; A61K 9/22; A61K 9/26; A61K 9/20; A61K 9/14

(52) U.S. Cl. ......................... 424/469; 424/466; 424/468; 424/43; 424/44; 424/452; 424/465; 424/484; 424/485; 424/486; 424/488

(58) Field of Search ................................. 424/466, 43, 44, 424/452, 465, 484, 485, 486, 488, 468, 469

(56) References Cited

U.S. PATENT DOCUMENTS

| | | |
|---|---|---|
| 3,574,820 | 4/1971 | Johnson et al. . |
| 3,976,764 | 8/1976 | Watanabe et al. . |

(List continued on next page.)

FOREIGN PATENT DOCUMENTS

| | | |
|---|---|---|
| 52691/98 | 1/1998 | (AU) . |
| 2 105 970 | 10/1997 | (ES) . |
| 2 699 076 | 6/1994 | (FR) . |

(List continued on next page.)

OTHER PUBLICATIONS

Iannuccelli, et al., International Journal of Pharmaceutics, vol. 174 (1998) pp. 47–54, 55–62.

Thanoo, et al., Journal of Pharmacy and Pharmacology, vol. 45 (1993) pp. 21–24.

Aithal, K.S. et al., "Preparation and evaluation of Alginate Microspheres containing Norfloxacin and Ciprofloxacin", Indian Journal of Pharm. Sci., 1997, 59(2) pp. 61–67.

Bakhouya, A. et al., "Calculation of the antibiotic level in the plasma with an oral erosion–controlled dosage form", International Journal of Pharmaceutics, 143 (1996) pp. 143–149.

"Declaration of Facts and Data Submitted for Consideration as Part of Information Disclosure Statement" by Tausif Monif dated Nov. 3, 2000.

*Primary Examiner*—Thurman K. Page
*Assistant Examiner*—Todd Ware
(74) *Attorney, Agent, or Firm*—Jayadeep R. Deshmukh, Esq.

(57) ABSTRACT

A pharmaceutical composition in the form of tablets or capsules provides a combination of temporal and spatial control of drug delivery to a patient for effective therapeutic results. The pharmaceutical composition comprises a drug, a gas generating component, a swelling agent, a viscolyzing agent, and optionally a gel forming polymer. The swelling agent belongs to a class of compounds known as superdisintegrants (e.g., cross-linked polyvinylpyrrolidone or sodium carboxymethylcellulose). The viscolyzing agent initially and the gel forming polymer thereafter form a hydrated gel matrix which entraps the gas, causing the tablet or capsule to be retained in the stomach or upper part of the small intestine (spatial control). At the same time, the hydrated gel matrix creates a tortuous diffusion path for the drug, resulting in sustained release of the drug (temporal control). A preferred once daily ciprofloxacin formulation comprises 69.9% ciprofloxacin base, 0.34% sodium alginate, 1.03% xanthan gum, 13.7% sodium bicarbonate, 12.1% cross-linked polyvinylpyrrolidone, and optionally other pharmaceutical excipients, the formulation being in the form of a coated or uncoated tablet or capsule.

11 Claims, 3 Drawing Sheets

U.S. PATENT DOCUMENTS

| | | |
|---|---|---|
| 4,036,228 | 7/1977 | Theeuwes . |
| 4,126,672 | 11/1978 | Sheth et al. . |
| 4,160,020 | 7/1979 | Ayer et al. ............................ 424/15 |
| 4,167,558 | 9/1979 | Sheth et al. . |
| 4,344,929 | 8/1982 | Bonsen et al. . |
| 4,414,198 | 11/1983 | Michaelson . |
| 4,434,153 | 2/1984 | Urquhart et al. . |
| 4,540,566 | 9/1985 | Davis et al. . |
| 4,588,726 | 5/1986 | Petersen et al. . |
| 4,610,870 | 9/1986 | Jain et al. . |
| 4,620,007 | 10/1986 | Grohe et al. . |
| 4,652,446 | 3/1987 | Dettmar . |
| 4,670,444 | 6/1987 | Grohe et al. . |
| 4,703,047 | 10/1987 | Petersen et al. . |
| 4,717,713 | 1/1988 | Zatz et al. . |
| 4,777,033 | 10/1988 | Ikura et al. . |
| 4,798,725 | 1/1989 | Patel . |
| 4,800,083 | 1/1989 | Hom et al. . |
| 4,814,178 | 3/1989 | Bolton et al. . |
| 4,814,179 | 3/1989 | Bolton et al. . |
| 4,839,171 | 6/1989 | Nelson ............................ 424/101 |
| 4,839,177 | 6/1989 | Colombo et al. ..................... 424/482 |
| 4,847,093 | 7/1989 | Ayer et al. . |
| 4,849,229 | 7/1989 | Gaylord et al. . |
| 4,886,669 | 12/1989 | Ventouras . |
| 4,931,285 | 6/1990 | Edgren et al. . |
| 4,965,252 | 10/1990 | Kuhrts ............................ 514/54 |
| 4,977,154 | 12/1990 | Sanchez et al. . |
| 4,980,353 | 12/1990 | Grohe et al. . |
| 4,981,854 | 1/1991 | Grohe et al. . |
| 4,992,449 | 2/1991 | Bitha et al. . |
| 4,994,276 | 2/1991 | Baichwal et al. . |
| 4,996,222 | 2/1991 | Carlin et al. . |
| 5,002,772 | 3/1991 | Curatolo et al. ..................... 424/438 |
| 5,007,790 | 4/1991 | Shell ............................ 424/451 |
| 5,015,479 | 5/1991 | Mulligan et al. . |
| 5,019,096 | 5/1991 | Fox, Jr. et al. . |
| 5,023,245 | 6/1991 | Kuhrts ............................ 514/54 |
| 5,023,257 | 6/1991 | Pollinger et al. . |
| 5,047,248 | 9/1991 | Calanchi et al. . |
| 5,051,262 | 9/1991 | Panoz et al. . |
| 5,096,714 | 3/1992 | Kuhrts . |
| 5,118,510 | 6/1992 | Kuhrts ............................ 424/451 |
| 5,128,142 | 7/1992 | Mulligan et al. . |
| 5,128,143 | 7/1992 | Baichwal et al. . |
| 5,133,090 | 7/1992 | Modak et al. . |
| 5,135,757 | 8/1992 | Baichwal et al. . |
| 5,152,986 | 10/1992 | Lange et al. . |
| 5,169,638 | 12/1992 | Dennis et al. ..................... 424/457 |
| 5,169,639 | 12/1992 | Baichwal et al. . |
| 5,178,878 | 1/1993 | Wehling et al. . |
| 5,188,839 | 2/1993 | Pearmain . |
| 5,198,229 | 3/1993 | Wong et al. . |
| 5,219,574 | 6/1993 | Wehling et al. . |
| 5,223,264 | 6/1993 | Wehling et al. . |
| 5,225,201 | 7/1993 | Beaurline . |
| 5,232,704 | 8/1993 | Franz et al. . |
| 5,256,699 | 10/1993 | Murphy et al. . |
| 5,271,946 | 12/1993 | Hettche . |
| 5,286,754 | 2/1994 | Streuff et al. . |
| 5,288,507 | 2/1994 | Sims et al. . |
| 5,292,518 | 3/1994 | Kuhrts . |
| 5,292,534 | 3/1994 | Valentine et al. . |
| 5,306,506 | 4/1994 | Zema et al. . |
| 5,340,572 | 8/1994 | Patel et al. . |
| 5,399,358 | 3/1995 | Baichwal et al. . |
| 5,415,871 | 5/1995 | Pankhania et al. . |
| 5,419,917 | 5/1995 | Chen et al. . |
| 5,425,950 | 6/1995 | Dandiker et al. . |
| 5,429,822 | 7/1995 | Gresser et al. . |
| 5,443,843 | 8/1995 | Curatolo et al. ..................... 424/464 |
| 5,445,826 | 8/1995 | Kuhrts . |
| 5,455,046 | 10/1995 | Baichwal . |
| 5,464,632 | 11/1995 | Cousin et al. . |
| 5,464,633 | 11/1995 | Conte et al. . |
| 5,466,469 | 11/1995 | Kuhrts ............................ 424/451 |
| 5,472,711 | 12/1995 | Baichwal . |
| 5,474,764 | 12/1995 | Patel et al. . |
| 5,478,574 | 12/1995 | Baichwal et al. . |
| 5,487,901 | 1/1996 | Conte et al. ..................... 424/472 |
| 5,503,846 | 4/1996 | Wehling et al. . |
| 5,512,297 | 4/1996 | Baichwal . |
| 5,518,730 | 5/1996 | Fuisz . |
| 5,534,263 | 7/1996 | Wong et al. . |
| 5,554,387 | 9/1996 | Baichwal . |
| 5,560,928 | 10/1996 | DeFelice . |
| 5,597,844 | 1/1997 | Chauhan et al. . |
| 5,612,053 | 3/1997 | Baichwal et al. . |
| 5,616,388 | 4/1997 | Tatsuno et al. . |
| 5,620,697 | 4/1997 | Törmälä et al. . |
| 5,624,677 | 4/1997 | El-Rashidi et al. . |
| 5,626,876 | 5/1997 | Muller et al. ..................... 424/484 |
| 5,631,004 | 5/1997 | Cagle et al. . |
| 5,639,476 | 6/1997 | Oshlack et al. . |
| 5,641,511 | 6/1997 | Kuhrts ............................ 424/451 |
| 5,650,169 | 7/1997 | Conte et al. ..................... 424/472 |
| 5,651,985 | 7/1997 | Penners et al. . |
| 5,662,933 | 9/1997 | Baichwal et al. . |
| 5,667,801 | 9/1997 | Baichwal . |
| 5,670,168 | 9/1997 | Baichwal et al. . |
| 5,681,583 | 10/1997 | Conte et al. . |
| 5,695,781 | 12/1997 | Zhang et al. . |
| 5,697,922 | 12/1997 | Thombre . |
| 5,725,880 | 3/1998 | Hirakawa et al. . |
| 5,728,401 | 3/1998 | Ahmed et al. . |
| 5,728,402 | 3/1998 | Chen et al. . |
| 5,738,865 | 4/1998 | Baichwal et al. . |
| 5,738,874 | 4/1998 | Conte et al. . |
| 5,773,019 | 6/1998 | Ashton et al. . |
| 5,773,025 | 6/1998 | Baichwal . |
| 5,780,057 | * 7/1998 | Conte et al. ..................... 424/468 |
| 5,807,580 | 9/1998 | Luber . |
| 5,811,126 | 9/1998 | Krishnamurthy . |
| 5,840,329 | 11/1998 | Bai . |
| 5,846,563 | 12/1998 | Baichwal . |
| 5,853,762 | 12/1998 | Myers et al. . |
| 5,858,412 | 1/1999 | Staniforth et al. . |
| 5,888,540 | 3/1999 | Sugden et al. . |
| 5,891,474 | 4/1999 | Busetti et al. ..................... 424/490 |

FOREIGN PATENT DOCUMENTS

| | | |
|---|---|---|
| 63-014715 | 1/1988 | (JP) . |
| 06024959 | * 2/1994 | (JP) . |
| WO 96/38174 | 12/1996 | (WO) . |
| WO 97/02020 | 1/1997 | (WO) . |
| WO 97/02021 | 1/1997 | (WO) . |
| WO 98/06385 | 2/1998 | (WO) . |
| WO 98/18610 | 5/1998 | (WO) . |
| WO 98/36732 | 8/1998 | (WO) . |
| WO 98/40401 | 9/1998 | (WO) . |

* cited by examiner

LINEAR PLOT OF MEAN SERUM CIPROFLOXACIN CONCENTRATIONS VERSUS TIME IN HEALTHY MALE HUMAN SUBJECTS

LINEAR PLOT OF PLASMA CIPROFLOXACIN CONCENTRATIONS VERSUS TIME IN HEALTHY MALE HUMAN SUBJECTS (N=12) (TEST FED VS. REFERENCE FED)

ORALLY ADMINISTERED CONTROLLED DRUG DELIVERY SYSTEM PROVIDING TEMPORAL AND SPATIAL CONTROL

BACKGROUND OF THE INVENTION

The present invention relates to a pharmaceutical composition in the form of tablets or capsules which provides a combination of spatial and temporal control of drug delivery to a patient for effective therapeutic results. The pharmaceutical composition comprises an active ingredient or drug, a gas generating component, a swelling agent, a viscolyzing agent, and optionally a gelling polymer. The swelling agent belongs to a class of highly absorbent compounds commonly referred to as superdisintegrants. This class of compounds includes, for example, cross-linked polyvinyl pyrrolidone and cross-linked sodium carboxymethylcellulose. The viscolyzing agent is a highly viscous material which upon contact with gastric fluid entraps the gas produced by the gas generating component. The viscolyzing agent consists of, for example, a carbohydrate gum. The gelling polymer is preferably a cross-linkable gelling polymer, such as a water soluble salt of one or more polyuronic acids, e.g., sodium alginate.

The improved controlled drug delivery system of the present invention is designed to deliver effectively a drug to a patient over a specific time period (temporal control) and from a particular portion of the patient's gastrointestinal tract (spatial control). The improved controlled drug delivery system avoids dose dumping and results in the most therapeutic administration of a particular drug to a person with a particular ailment.

It is well known to those skilled in the art that for ailments requiring multiple doses of a particular drug, the blood levels of a drug need to be maintained above its minimum effective level and below its minimum toxic level in order to obtain the desired therapeutic effects, to avoid undesired toxic effects, and to minimize side effects. When the blood levels of a drug are in this range, the drug is eliminated from the body at a particular rate. A controlled drug delivery system is usually designed to deliver the drug at this particular rate; safe and effective blood levels are maintained for a period as long as the system continues to deliver the drug at this rate. Controlled drug delivery usually results in substantially constant blood levels of the active ingredient as compared to the uncontrolled fluctuations observed when multiple doses of quick releasing conventional dosage forms are administered to a patient. Controlled drug delivery results in optimum therapy, and not only reduces the frequency of dosing, but may also reduce the severity and frequency of side effects.

The above basic concepts of controlled drug delivery are well known to those skilled in the art. Considerable efforts have been made in the last decades to develop new pharmaceutically viable and therapeutically effective controlled drug delivery systems. Attention has been focused particularly on orally administered controlled drug delivery systems because of the ease of administration via the oral route as well as the ease and economy of manufacture of oral dosage forms such as tablets and capsules. A number of different oral controlled drug delivery systems based on different release mechanisms have been developed. These oral controlled drug delivery systems are based on different modes of operation and have been variously named, for example, as dissolution controlled systems, diffusion controlled systems, ion-exchange resins, osmotically controlled systems, erodible matrix systems, pH-independent formulations, swelling controlled systems, and the like.

An orally administered controlled drug delivery system encounters a wide range of highly variable conditions, such as pH, agitation intensity, and composition of the gastrointestinal fluids as it passes down the gastrointestinal tract. Ideally, an oral controlled drug delivery system will deliver the drug at a constant and reproducible rate in spite of the varying conditions. Considerable efforts have therefore been made to design oral controlled drug delivery systems that overcome these drawbacks and deliver the drug at a constant rate as it passes down the gastrointestinal tract.

It is well known to those skilled in the art that a drug may not be absorbed uniformly over the length of the gastrointestinal tract, and that drug absorption from the colon is usually erratic and inefficient. Also, certain drugs are absorbed only from the stomach or the upper parts of the small intestine. Furthermore, an important factor which may adversely affect the performance of an oral controlled drug delivery system is that the dosage form may be rapidly transported from more absorptive upper regions of the intestine to lower regions where the drug is less well absorbed. Therefore, in instances where the drug is not absorbed uniformly over the gastrointestinal tract, the rate of drug absorption may not be constant in spite of the drug delivery system delivering the drug at a constant rate into the gastrointestinal fluids. More particularly, in instances where a drug has a clear cut "absorption window," i.e., the drug is absorbed only from specific regions of the stomach or upper parts of the small intestine, it may not be completely absorbed when administered in the form of a typical oral controlled drug delivery system. It is apparent that for a drug having such an "absorption window," an effective oral controlled drug delivery system should be designed not only to deliver the drug at a controlled rate, but also to retain the drug in the upper parts of the gastrointestinal tract for a long period of time.

An oral controlled drug delivery system is described by Stockwell, A. F., et al., in *Journal Controlled Release*, 3, 167–175 (1986), who disclosed a hydrocolloid calcium gelled alginate formulation which includes sodium bicarbonate. This composition was investigated by Ingani et al., in *Int. J. Pharm.*, 35, 157–164 (1987), who found that the bioavailability of riboflavin was increased as compared to a standard system. However, it is known that the use of alginate alone presents difficulties in tabletting, film coating, and storage.

U.S. Pat. No. 4,777,033, assigned to Teijin Limited, discloses an oral controlled release pharmaceutical composition comprising a lower alkyl ether of cellulose, polyacrylic acid or its pharmaceutically acceptable salt, a drug, and an effective amount of an effervescent foaming agent. The composition is intended to be retained in the stomach for a long time and to deliver the drug at a slow, controlled rate in order to exert its therapeutic effect for many hours. The compositions exemplified therein are either in the form of granules, granules filled in capsules, or tablets that break up into granules when subjected to the dissolution test specified in the Japanese Pharmacopoeia.

It is well accepted by those skilled in the art that granules are dissolved in a relatively shorter time than intact tablets because of their smaller size and increased surface area. Consequently, granules usually release drug in a shorter gastrointestinal transit time than intact tablets and are not well suited for a well-defined controlled drug delivery system. Thus, the composition disclosed in U.S. Pat. No. 4,777,033 which breaks up into granules does not provide the desired prolonged retention time at the site of absorption. A drug which is absorbed only from upper parts of the gastrointestinal tract would then be incompletely absorbed. Also, upon disintegration, a tablet yields a large number of granules and it is now recognized by those skilled in the art that multiparticulate systems, such as pellets or granules, are distributed over the length of the gastrointestinal tract releasing the drug at these different locations. Thus, the composition of U.S. Pat.. No. 4,777,033 may not release the drug specifically in the upper parts of the gastrointestinal tract. Additionally, it may be difficult to obtain the desired rate of release for a drug that has a high water solubility. The rapid release of a large quantity of such a highly soluble drug, i.e., a dose dumping effect, is particularly undesirable in controlled drug delivery systems because such formulations contain several times the amount of drug in a conventional formulation.

Japanese Patent No. 63-14715, assigned to Zeria Pharmaceutical Co., discloses a slow releasing pharmaceutical oral formulation comprising a high viscosity water soluble polymer, cross-linked insoluble polyvinylpyrrolidone, and a foaming component. The system is intended to release the drug slowly into the stomach. In the systems exemplified, the water soluble polymer includes cellulose derivatives or polyvinyl alcohol. For such systems sufficient quantities of water soluble polymers are required to prevent disintegration of the tablets into granules. Thus, when a high dose medicament is to be incorporated into tablets based on this system, the size of the tablets would be large.

U.S. Pat. No. 5,651,985, assigned to Bayer AG, discloses a composition comprising a pharmacologically active compound, a pharmaceutically acceptable auxiliary, polyvinylpyrrolidone, and a methacrylic acid polymer having an acidic number between 100 and 1200 mg of KOH/g of polymer solid substance. Optionally, the composition also contains a gas forming additive. The composition absorbs many times its weight of acidic water and forms a highly swollen gel of high mechanical and dimensional stability. The gel forming agent should be sufficient so that after administration it can swell up to a size which prevents passage through the pylorous for a relatively long time. At least 30% by weight and up to 90% by weight of the composition comprises the polymers, and thus dosage forms containing a high dose medicament would be large and inconvenient for oral administration.

Accordingly, none of the oral controlled drug delivery systems heretofore described is completely satisfactory.

OBJECTS OF THE PRESENT INVENTION

It is an object of the present invention to provide a pharmaceutical composition in the form of tablets or capsules which constitutes an oral controlled drug delivery system that:

a. generates and entraps a gas in a hydrated matrix upon contact with an aqueous medium or gastric fluids, and which retains a substantially monolithic form in the stomach, b. provides increased gastric residence and thereby a longer period of residence of the drug delivery system in the gastrointestinal tract, c. delivers the drug at a controlled rate such that the drug is delivered over a period of time which is the same as or less than the period of residence of the delivery system in the absorptive regions of the gastrointestinal tract, and d. provides, as compared to other oral controlled drug delivery systems, increased absorption of a drug that is absorbed largely from the upper parts of the gastrointestinal tract.

It is also an object of the present invention to provide a pharmaceutical composition constituting an oral controlled drug delivery system that maintains its physical integrity, i.e., remains intact or substantially gains a monolithic form when contacted with an aqueous medium, even when the quantity of medicaments is large, and wherein the proportion of polymers is small compared to other components of the system. It is a further object of the present invention to provide a drug delivery system that incorporates a high dose medicament without the loss of any of its desirable attributes, as listed above, such that the system is of an acceptable size for oral administration.

SUMMARY OF THE INVENTION

The present invention provides a novel pharmaceutical composition in the form of tablets or capsules which composition constitutes an orally administered controlled drug delivery system. The pharmaceutical composition comprises a drug, a gas generating component, a swelling agent (e.g., cross-linked polyvinylpyrrolidone or cross-linked sodium carboxymethylcellulose) a viscolyzing agent (e.g., a carbohydrate gum), and (optionally) a gel forming polymer (e.g., sodium alginate). Optionally further, the novel pharmaceutical composition also contains an additional hydrophilic water soluble polymer (e.g., hydroxypropyl methylcellulose).

Preferably, the inventive oral controlled drug delivery system which is a pharmaceutical composition in the form of tablets or capsules comprises at least one drug, about 5 to about 50% by weight of the gas generating component, about 5 to about 50% by weight of the swelling agent, about 0.1 to about 30% by weight of the viscolyzing agent, and about 0.1 to about 20% by weight of the gel forming polymer. The pharmaceutical composition may also contain about 0.5 to about 20% by weight of the additional hydrophilic water soluble polymer.

A pharmaceutical composition having such a combination of ingredients has not been disclosed earlier. Such a pharmaceutical composition is referred to herein at times as a Controlled Gas Powered System (CGPS).

The swelling agents used herein (cross-linked polyvinylpyrrolidone or cross-linked sodium carboxy methylcellulose) belong to a class of compounds known as super-disintegrants which usually function to promote disintegration of a tablet by absorbing large amounts of water and thereby swelling. This expansion, as well as hydrostatic pressure, cause the tablet to burst. In a tablet which also contains a gas generating component (which may actually be a gas generating couple), one would expect the tablet to disintegrate instantly upon contact with aqueous fluid, if not blow apart. Remarkably, it has been found that in the presence of an instantly acting viscolyzing agent, the generated gas is entrapped and the superdisintegrant acts as a swelling agent which swells to, preferably, at least twice its original volume. Thus, the combination of the gas generating component, the swelling agent which is actually a superdisintegrant, and the viscolyzing agent permit the Controlled Gas Powered System to act as a controlled drug delivery system. Additionally, with the passage of time, the gel forming polymer produces a cross-linked three-dimensional molecular network resulting in a hydrodynamically balanced system that is retained in the stomach and releases the drug over a sustained period of time.

Surprisingly, it has been found that the Controlled Gas Powered System of the present invention is retained for longer periods of time in the stomach (spatial control) than previously known hydrophilic matrix tablets, floating capsules and bioadhesive tablets when these systems are administered with food. Thus, the longer period of gastric retention as compared to other oral controlled drug delivery systems can be attributed to the use of the Controlled Gas Powered System as herein described. The Controlled Gas Powered System results in release of the drug into the more absorptive regions of the gastrointestinal tract, i.e., into the stomach and the small intestine rather than into the large intestine where drug absorption is poor or erratic. Thus, one may expect that if the drug is released at a constant and controlled rate, it will also be absorbed at a more or less constant rate.

Even more surprisingly, it has been found that even for a drug that is absorbed only from the upper gastrointestinal tract, i.e., from the stomach down to the jejunum, the Controlled Gas Powered System provides the desired absorption at a rate such that effective plasma levels are maintained for a prolonged duration and the system is suitable for once-daily administration (temporal control). Moreover, the system provides increased absorption of the drug as compared to other oral controlled drug delivery systems such as hydrophilic matrix tablets and floating capsules. This is achieved by adjusting the time period of release for the drug so that it is about the same as or less than the retention time of the tablets at the site of absorption. Thus, the system is not transported past the "absorption window" prior to releasing all of the drug, and maximum bioavailability is attained.

In a preferred embodiment of the invention, a once daily formulation for the controlled release of ciprofloxacin comprises a pharmaceutically effective amount of ciprofloxacin, about 0.2% to about 0.5% sodium alginate, about 1.0% to about 2.0% xanthan gum, about 10.0% to about 25% sodium bicarbonate, and about 10.0% to about 25% cross-linked polyvinylpyrrolidone, the percentages being w/w percentages of the composition, wherein the weight ratio of sodium alginate to xanthan gum is between about 1:1 and about 1:10. The foregoing formulation may be in the form of a tablet or capsule, and may be coated with a film forming polymer or a pharmaceutical excipient.

DETAILED DESCRIPTION OF THE INVENTION

Figure 1:
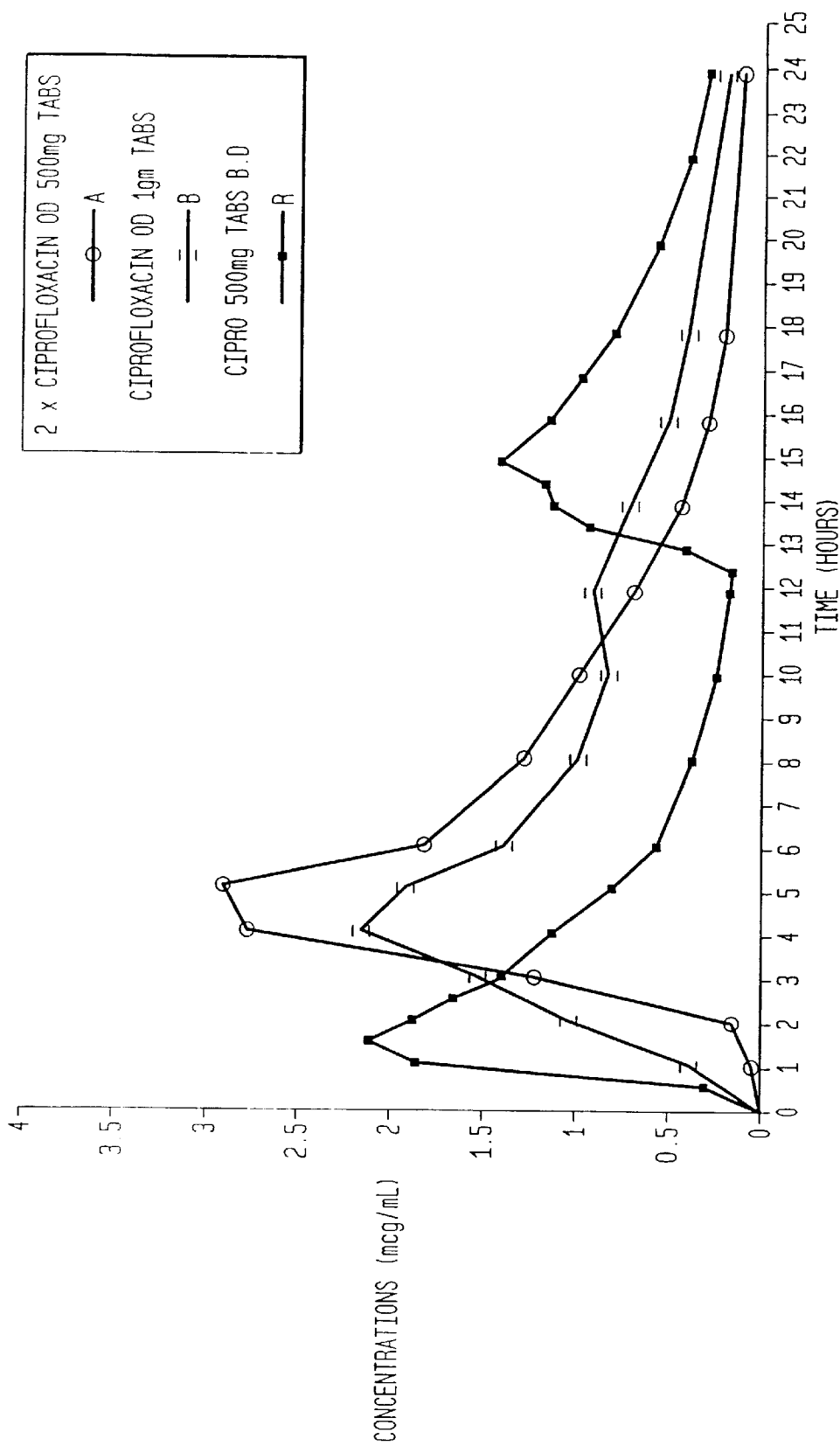
FIG. 1 is a graph illustrating mean serum concentration vs. time for the drug ciprofloxacin free base (Table 3) and ciprofloxacin HCl (Table 1) when incorporated in the oral controlled drug delivery system as compared to the presently marketed Cipro™ (Bayer Corp.) immediate release tablets.

According to the present invention, the Controlled Gas Powered System (CGPS) includes a swelling agent, a gas entrapping viscolyzing agent, and optionally a gel forming polymer. Together these components form a hydrated gel matrix. The CGPS further contains a gas generating component such that a gas (generally $CO_2$ but in some cases $SO_2$) is generated in a controlled manner and is entrapped in the hydrated gel matrix. The swelling agent which belongs to the class of compounds known as superdisintegrants, absorbs large amounts of fluid and causes the matrix to swell significantly. The gas generated by the gas generating component also causes matrix expansion. However, in the present invention, swelling of the matrix is controlled by the viscolyzing agent, which acts both as a swellability and a drug release controlling agent.

The characteristics of the hydrated gel matrix can be modified by altering the ratios and amounts of the swelling agent, the viscolyzing agent, the gas generating component, and the optionally included gelling polymer without loss of physical integrity of the hydrated gel system. The composition can thus be designed to obtain the optimal rate of release of the drug. It has also been found that such a composition when administered with food is retained for longer periods in the stomach, and thereby in the gastrointestinal tract without loss of its physical integrity.

The generated gas influences the drug delivery from the tablets or capsules in ways that are currently not well understood. For example, factors that may influence drug delivery include:

a. the presence of entrapped gas within the matrix can affect the diffusion path length of the drug and thus exerts a release-controlling effect;

b. the presence of entrapped gas within the matrix can affect the rate of surface erosion of the hydrated gel matrix and thus exerts both a hydrodynamic and a release controlling effect;

c. the expanding pressure and the presence of the gas affects the internal structure of the hydrated gel and thus exerts both a hydrodynamic and a release controlling effect;

d. the presence of entrapped gas and its expanding pressure affects the influx of the acidic gastric fluid through the pores of the matrix and thus exerts a release-controlling effect;

It should be realized that gas generated in a small volume within the matrix can exert a high pressure. If this exceeds the capillary pressure due to the surface tension of the aqueous fluid, then it will cause the aqueous fluid in a pore to be pushed by the gas allowing the gas to expand until the internal gas pressure equals the capillary pressure. This phenomenon thus would affect the rate of hydration of the matrix and have a role in determining the rate of release of the drug. In systems which cross-link, it will also have an influence on the developing gel structurization.

The various components of the novel Controlled Gas Powered System (CGPS) will now be described in more detail.

DRUG

According to the present invention, the pharmaceutical composition is in the form of tablets or capsules that provide a controlled rate of delivery (i.e., temporal control) of at least one therapeutically active ingredient or drug. The drug may be pharmacologically or chemotherapeutically active itself, or may be converted into a pharmacologically or chemotherapeutically active species by a chemical or enzymatic process in the body. The drug can be any drug for which therapy or chemotherapy would be improved as a result of controlled drug delivery. Examples of suitable drugs include antibiotics, anti-cancer, anti-fungals, anti-fibrial, and anti-viral agents. The present invention is particularly suitable for controlled rate of delivery of a drug that does not show uniform absorption characteristics throughout the length of the gastrointestinal tract.

The novel pharmaceutical composition is more particularly suitable for controlled delivery of drugs that are absorbed only from the upper parts of the gastrointestinal tract with a specific absorption window (i.e., spatial control), for example, ciprofloxacin which is absorbed only from the region extending from the stomach to the jejunum. The pharmaceutical composition is also suitable for drugs that are absorbed by a saturable transport process because the drug is released in the upper parts of the gastrointestinal tract at a slow rate such that the transport process is not saturated and maximum bioavailability can be attained. In these cases, the system is not transported past the "absorption window" prior to releasing all the drug so that maximum bioavailability can be attained.

Illustrative examples of drugs that are suitable for the present invention include antibacterial/anti-infective agents, such as ciprofloxacin, cefuroxime, cefatrizine, cefpodoxime, clarithromycin, loracarbef, azithromycin, cefixime, cefadroxil, amoxycillin, and the like; antivirals, such as acyclovir; cardiovascular agents, such as diltiazem, captopril, and the like; lipid lowering agents, such as simvastatin, lovastatin and the like; non-steroidal anti-inflammatory agents, such as etodolac, ketorolac, and the like; anti-ulcer agents, such as ranitidine, famotidine, and the like; drugs for respiratory diseases, such as fexofenadine, pseudoephedrine, phenylpropanolamine, dextromethorphan, chlorpheniramine, and the like; dopaminergic agents, such as bromocriptine; immunosuppressants, such as cyclosporin; skeletal muscle relaxants, such as baclofen; anti-gout agents, such as allopurinol; and the like. The drug itself or its pharmaceutically acceptable salt or ester may be used in the present invention. Moreover, combinations of drugs that are typically administered together may be included as the drug component of the pharmaceutical composition. The amount of drug to be used in the composition is that which is typically administered for a given period of time. According to the present invention, the pharmaceutical composition can incorporate a high dose medicament. Accordingly, the amount of drug to be used in the present invention typically ranges from about 0.5 mg up to about 1200 mg.

GAS GENERATING COMPONENT

The gas generating component may consist of a single substance known to produce gas upon contact with gastric fluid, or may consist of a gas generating couple. Examples of the gas generating component that may be used in the present invention include carbonates, such as calcium carbonate or sodium glycine carbonate, bicarbonates such as sodium hydrogen carbonate or potassium hydrogen carbonate, sulfites, such as sodium sulfite, sodium bisulfite, or sodium metabisulfite, and the like.

In those embodiments of the present invention where the pharmaceutical composition also contains a water soluble salt of one or more polyuronic acids (e.g., sodium alginate) as the gelling polymer, the gas generating component preferably should not include salts of calcium.

The gas generating component interacts with an acid source triggered by contact with water or simply with gastric fluid to generate carbon dioxide or sulfur dioxide that gets entrapped within the hydrated gel matrix of the swelling composition. The gas generating component such as carbonates and bicarbonates may be present in amounts from about 5% to about 50%, preferably from about 10% to about 30%, by weight of the composition. These salts can be used alone or in combination with an acid source as a couple. The acid source may be one or more of an edible organic acid, a salt of an edible organic acid, or mixtures thereof. Examples of organic acids that may be used as the acid source in the present invention include, for example: citric acid or its salts such as sodium citrate or calcium citrate; malic acid, tartaric acid, succinic acid, fumaric acid, maleic acid, or their salts; ascorbic acid or its salts such as sodium or calcium ascorbate; glycine, sarcosine, alanine, taurine, glutamic acid, and the like. The organic acid salts that may be used as the acid source in the present invention include, for example, a mono-alkali salt of an organic acid having more than one carboxylic acid functional group, a bialkali metal salt of an organic acid having more than two carboxylic acid functional groups, and the like. The acid source may be present in an amount from about 0.5% to 15% by weight, preferably from about 0.5% to about 10% by weight, and more preferably from about 0.5% to about 5% by weight, of the total weight of the composition.

SWELLING AGENT

According to the present invention, the pharmaceutical composition contains a swelling agent which is capable of swelling to greater than its original volume and preferably to at least twice its original volume when coming into contact with a aqueous fluid, such a gastrointestinal fluid. Examples of swelling agents that may be used in the present invention include cross-linked polyvinylpyrrolidone, cross-linked carboxymethylcellulose sodium, sodium starch glycolate, and the like. These compounds belong to the class of compounds known as superdisintegrants. Preferably, the swelling agent is cross-linked carboxymethylcellulose or cross linked polyvinylpyrrolidone. The swelling agent, which normally swells to several times its original volume in water, exhibits a controlled swelling in the presence of the viscolyzing agent. The swelling agent may be present in an amount from about 5% to about 50%, preferably from about 10% to about 30%, and more preferably from about 10% to about 20%, by weight of the total weight of the composition.

VISCOLYZING AGENT

According to the present invention, the pharmaceutical composition contains a viscolyzing agent which, upon contact with gastrointestinal fluid, instantaneously viscolyzes to trap the gas generated by the gas generating component. Preferably, the viscolyzing agent comprises of a carbohydrate gum. Examples of carbohydrate gums that may be used in the present invention include xanthan gum, tragacanth gum, gum karaya, guar gum, acacia, and the like. In the present invention, it has been found that a carbohydrate gum helps in maintaining tablet integrity when stirred in an aqueous medium, and in sustaining the release of the drug even when its concentration is low (below 10% by weight) to very low (below 3% by weight). When the present invention is in the form of capsules, the pharmaceutical composition upon being agitated in an aqueous medium forms a non-disintegrating capsule-shaped plug which maintains its physical integrity.

The successful use of even low amounts of a viscolyzing agent such as a carbohydrate gum in providing tablet integrity is indeed surprising in view of the fact that the pharmaceutical composition of the present invention contains a gas generating component and a swelling agent which is most frequently employed as a disintegrant. Those skilled in the art can well recognize that both components can result in rapid disintegration of tablets. Tablets containing hydroxypropylcellulose in amounts approximately the same as the amounts of carbohydrate gum in the present invention disintegrate in 10 to 15 minutes when stirred in an acidic medium. Such disintegration can result in a dose dumping effect, i.e., rapid delivery of a large quantity of drug from the system, and is undesirable particularly because controlled drug delivery systems contain several times the amount of drug in a conventional formulation. Granules formed as a result of the disintegration are also emptied from the stomach in a shorter time than intact tablets. The present invention avoids such disintegration with the use of small quantities of a viscolyzing agent, such as a heteropolysaccharide gum, so that tablets or capsules containing a high dose medicament are of an acceptable size to be taken orally.

In preferred embodiments of the present invention, the viscolyzing agent is xanthan gum. Xanthan gum, also known as corn sugar gum, is a high molecular weight (ca. $2 \times 10^6$) biosynthetic polysaccharide gum produced by a pure-culture aerobic fermentation of a carbohydrate with *Xanthomonas campestris*. It is extraordinarily enzymatically resistant.

In preferred embodiments of the present invention, the xanthan gum has a particle size such that at least 50% by weight passes through a sieve with 44 µm mesh aperture (Sieve No. 325, ASTM). In more preferred embodiments, the xanthan gum has a particle size such that all of it passes through a 44 µm mesh aperture (Sieve No. 325, ASTM).

Generally, the viscolyzing agent is present in an amount from about 0.1% to about 30% by weight of the total weight of the composition, preferably from about 0.1% to about 10%, and more preferably from about 0.1% to about 7%, by weight of the total weight of the composition.

GEL FORMING POLYMER

According to the present invention, the pharmaceutical composition optionally contains a gel forming polymer which is preferably a, water soluble salt of one or more polyuronic acids. The gel forming polymer cross-links with time to form a stable structure which entraps the generated gas. Thus, with the passage of time, the gel forming polymer results in a hydrodynamically balanced system whereby the matrix is retained in the stomach for an extended period of time. Simultaneously, the viscolyzing agent and gel forming polymer provide a tortuous diffusion pathway for the drug, thereby resulting in controlled drug release. Examples of water soluble salts of polyuronic acid that may be used in the present invention include alkali metal salts of alginic acid, alkali metal salts of pectic acid, and the like. In preferred embodiments of the present invention, the water soluble salt of polyuronic acid is a salt of alginic acid, which is actually a mixture of two polyuronic acids, namely, mannuoronic acid and guluronic acid. Examples of alkali metal salts of alginic acid that may be used in the present invention include sodium alginate, potassium alginate, ammonium alginate, and the like. A mixture of the same or different alginic acid salts of the same or different viscosities may be used.

According to the present invention, when the pharmaceutical composition contains a water soluble salt of one or more polyuronic acids preferably a salt of alginic acid, it should be free of calcium ions. Accordingly, the pharmaceutical composition of the present invention should not contain calcium alginate. It is found that the presence of a salt of alginic acid improves the entrapment of gas within the matrix. Alginate salts can also modify the rate at which a drug is released into acidic gastric fluids from matrices containing a carbohydrate gum.

Generally, the gel forming polymer, such as a salt of alginic acid, is present in an amount from about 0.1% to about 20%, preferably from 0.1% to about 10%, and most preferably from about 0.5% to about 5%, by weight of the total weight of the composition.

HYDROPHILIC WATER SOLUBLE POLYMER

According to the present invention, the pharmaceutical composition may also contain a hydrophilic water soluble polymer in addition to the salt of polyuronic acid. Examples of a hydrophilic water soluble polymer that may be included in the composition of the present invention include hydroxypropyl methylcellulose, hydroxypropylcellulose, polyacrylic acid, and the like. In one preferred embodiment, the hydrophilic polymer is a cross-linked polyacrylic acid polymer such as is available under the brand name Carbopol (B. F. Goodrich, U.S.A.). These hydrophilic polymers are useful in the present invention in modifying the rate of release of the drug from the composition.

The hydrophilic polymer may be present in an amount from about 0.5% to about 20%, preferably from about 0.5% to about 10%, and more preferably from about 0.5% to about 5%, by weight of the total weight of the composition.

OTHER EXCIPIENTS

The pharmaceutical composition may also contain other conventional pharmaceutical excipients, for example, water soluble diluents such as lactose, dextrose, mannitol, sorbitol, and the like; water insoluble diluents such as starch, microcrystalline cellulose, powdered cellulose, and the like; or lubricants such as talc, stearic acid or its salt, magnesium stearate, and the like. According to the present invention, when the pharmaceutical composition contains a water soluble salt of one or more polyuronic acids, the other pharmaceutical excipients preferably should be free of calcium ions.

PROCESS FOR PREPARATION

According to the present invention, the pharmaceutical composition is prepared by mixing the drug with the gas generating component, the swelling agent, the gas entrapping viscolyzing agent and the optionally included gel forming polymer, plus other excipients and lubricants. The blend is directly compressed into tablets or may be filled into capsules. Alternatively, the pharmaceutical composition is prepared by mixing the foregoing ingredients with only one-half of the lubricants. The mixture is roll compacted and then sieved to obtain granules. The granules are then mixed with the remaining lubricants, and filled into capsules or compressed into tablets.

COATING

According to the present invention, when the pharmaceutical composition is in the form of tablets, it may be coated with a thin layer of a rapidly dissolving water soluble polymer or pharmaceutical excipient. A coating of a water soluble excipient results in faster hydration and gas formation than a coating of water soluble polymer and is the preferred coating. In cases where a polymeric coating is required, a low molecular weight, low viscosity polymer is the preferred material.

Examples of water soluble pharmaceutical excipients include lactose, sucrose, dextrose, mannitol, xylitol, and the like. In a preferred embodiment of the present invention, the water soluble excipient used as a coating is lactose.

The tablets may be coated to a weight build-up of about 1% to about 4%, preferably, about 1% to about 2%. The coating also helps in masking any bitter taste associated with the drug.

The present invention is illustrated by, but is by no means limited to, the following examples:

EXAMPLE 1

This example illustrates the present invention when the active ingredient is ciprofloxacin hydrochloride. Ciprofloxacin is an example of a drug which is absorbed only from the upper part of the intestine. The pharmaceutical composition is given in Table 1.

TABLE 1

| Ingredient | Weight (mg/tablet) | % w/w |
|---|---|---|
| Ciprofloxacin hydrochloride monohydrate | 598.47 | 55.16 |
| Xanthan Gum (Keltrol TF) | 20.00 | 1.84 |
| Sodium alginate (Keltone LVCR) | 15.00 | 1.38 |
| Cross-linked carboxymethylcellulose (Ac-Di-Sol) | 110.00 | 10.14 |
| Sodium bicarbonate | 230.00 | 21.20 |
| Microcrystalline cellulose (Avicel PH 101) | 16.53 | 1.52 |
| Sodium Chloride | 25.0 | 2.30 |
| Citric Acid | 20.0 | 1.84 |
| Cross-linked polyacrylic acid (Carbopol 971P) | 10.0 | 0.93 |
| Talc | 10.00 | 0.93 |
| Magnesium Stearate | 20.00 | 1.84 |
| Aerosil | 10.00 | 0.93 |
| Total | 1085.00 | 100% |

Ciprofloxacin, xanthan gum, sodium alginate, cross-linked carboxymethylcellulose, sodium bicarbonate, microcrystalline cellulose, sodium chloride, citric acid, and half of the lubricants were mixed together and sieved through a sieve (British Standard Sieve (BSS) No. 44). The blend was compacted on a roll-compactor and the compact sieved through a sieve (BSS No. 22) to obtain granules. The granules were mixed with the remaining lubricants and Carbopol and then compressed into tablets. The tablets were spray coated with an aqueous coating composition containing 15.8% w/w lactose, 3.18% w/w talc, and 1.587% w/w titanium dioxide to a weight build up of 1% to 1.5%.

The tablets were tested for dissolution in 0.1 N HCl using USP Apparatus 1 with basket speed at 100 rpm. The dissolution results are given in Table 2.

TABLE 2

| Time (hrs) | Cumulative Percent Release |
|---|---|
| 1 | 21.16 |
| 2 | 33.22 |
| 4 | 58.72 |
| 6 | 74.6 |
| 8 | 85.83 |
| 10 | 93.58 |

EXAMPLE 2

This example illustrates the present invention when the active ingredient is ciprofloxacin base. The pharmaceutical composition is given in Table 3.

TABLE 3

| Ingredient | Weight (mg/tablet) | % w/w of tablet | % w/w of drug |
|---|---|---|---|
| Ciprofloxacin base | 1000.00 | 71.43 | 100.0 |
| Xanthan Gum (Keltrol TF) | 15.00 | 1.07 | 1.5 |
| Sodium alginate (Keltone LVCR) | 10.00 | 0.71 | 1.0 |
| Cross-linked polyvinylpyrrolidone (Kollidon CL-M) | 150.00 | 10.71 | 15.0 |
| Sodium bicarbonate | 200.00 | 14.28 | 20.0 |
| Magnesium Stearate | 15.00 | 1.07 | 1.5 |
| Talc | 10.00 | 0.71 | 10.0 |
| Total | 1400.00 | 100 | — |

The tablets were prepared and tested for dissolution as described in Example 1. The dissolution results are given in Table 4.

TABLE 4

| Time (hrs) | Cumulative Percent Release |
|---|---|
| 1 | 24.9 |
| 2 | 37.8 |
| 4 | 60.5 |
| 6 | 80.6 |
| 8 | 85.4 |
| 10 | 98.8 |

EXAMPLE 3

This example illustrates the present invention when the active ingredient is ciprofloxacin hydrochloride. The pharmaceutical composition is given in Table 5.

TABLE 5

| Ingredient | Weight (mg/tablet) | % w/w |
|---|---|---|
| Ciprofloxacin hydrochloride monohydrate | 600.00 | 61.54 |
| Xanthan Gum (Keltrol TF) | 10.00 | 1.02 |
| Sodium alginate (Keltone LVCR) | 25.00 | 2.57 |
| Cross-linked carboxymethylcellulose (Ac-Di-Sol) | 60.00 | 6.16 |
| Sodium bicarbonate | 250.00 | 25.64 |
| Microcrystalline cellulose (Avicel PH 101) | 15.00 | 1.54 |
| Talc | 5.00 | 0.52 |
| Magnesium Stearate | 10.00 | 1.02 |
| Total | 975.00 | 100% |

The tablets were prepared as described in Example 1 except that Ac—Di—Sol was incorporated extragranularly. Tablets were tested for dissolution as described in Example 1. The dissolution results are given in Table 6.

TABLE 6

| Time (hrs) | Cumulative Percent Release |
|---|---|
| 1 | 28.16 |
| 2 | 38.32 |
| 4 | 52.37 |
| 6 | 64.03 |
| 8 | 74.23 |
| 10 | 82.80 |

EXAMPLE 4

This example illustrates the present invention when the active ingredient is acyclovir. Tablets were prepared according to the composition given in Table 7.

TABLE 7

| Ingredient | Weight (mg/tablet) | % w/w |
|---|---|---|
| Acyclovir | 525.00 | 69.54 |
| Xanthan Gum (Keltrol TF) | 35.00 | 4.64 |
| Sodium alginate (Keltone LVCR) | 25.00 | 3.31 |
| Cross-linked polyvinylpyrrolidone (Kollidon CL-M) | 80.00 | 10.60 |
| Sodium bicarbonate | 75.00 | 9.93 |
| Magnesium Stearate | 8.00 | 1.06 |
| Talc | 7.00 | 0.93 |
| Total | 755.00 | 100% |

Tablets were prepared and tested for dissolution as described in Example 1. The dissolution results are given in Table 8.

TABLE 8

| Time (hrs) | Cumulative Percent Release |
|---|---|
| 1 | 24.68 |
| 2 | 33.42 |
| 4 | 43.02 |
| 7 | 51.52 |

EXAMPLE 5

This example illustrates the present invention in capsule form when the active ingredient is acyclovir. The pharmaceutical composition is given in Table 9.

TABLE 9

| Ingredient | Weight (mg/tablet) | % w/w |
|---|---|---|
| Acyclovir | 400.00 | 69.55 |
| Xanthan Gum (Keltrol TF) | 26.65 | 4.64 |
| Sodium alginate (Keltone LVCR) | 19.04 | 3.32 |
| Cross-linked polyvinylpyrrolidone (Kollidon CL-M) | 60.93 | 10.60 |
| Sodium bicarbonate | 57.12 | 9.93 |
| Magnesium Stearate | 6.09 | 1.06 |
| Talc | 5.33 | 0.93 |
| Total | 575.16 | 100% |

Acyclovir, xanthan gum, sodium alginate, cross-linked polyvinyl pyrrolidone, sodium bicarbonate, and half of the lubricants were passed through a sieve (BSS No. 44) and slugged using 16 mm punches and the slugs were passed through a sieve (BSS No. 22). The granules were mixed with the remaining half of the lubricants and filled into capsules. The capsules were tested for dissolution as described in Example 1. The dissolution results are given in Table 10.

TABLE 10

| Time (hrs) | Cumulative Percent Release |
|---|---|
| 1 | 9.52 |
| 2 | 16.48 |
| 4 | 24.82 |
| 6 | 34.42 |
| 8 | 42.38 |
| 10 | 51.20 |

EXAMPLE 6

This example illustrates the present invention when the active ingredient is diltiazem hydrochloride. The pharmaceutical composition is given in Table 11.

TABLE 11

| Ingredient | Weight (mg/tablet) | % w/w |
|---|---|---|
| Diltiazem Hydrochloride | 240.00 | 41.52 |
| Xanthan Gum (Keltrol TF) | 160.00 | 27.68 |
| Sodium alginate (Keltone LVCR) | 80.00 | 13.85 |
| Cross-linked polyvinylpyrrolidone (Kollidon CL-M) | 40.00 | 8.65 |
| Sodium bicarbonate | 50.00 | 6.92 |
| Magnesium Stearate | 4.00 | 0.69 |
| Talc | 4.00 | 0.69 |
| Total | 578.00 | 100% |

Tablets were prepared and tested for dissolution as described in Example 1. The dissolution results are given in Table 12.

TABLE 12

| Time (hrs) | Cumulative Percent Release |
|---|---|
| 1 | 12.60 |
| 2 | 19.23 |
| 4 | 29.87 |
| 6 | 39.33 |
| 10 | 54.43 |
| 12 | 60.50 |
| 15 | 68.80 |

EXAMPLE 7

This example illustrates the present invention when the active ingredient is diltiazem hydrochloride. The pharmaceutical composition is given in Table 13.

TABLE 13

| Ingredient | Weight (mg/tablet) | % w/w |
|---|---|---|
| Diltiazem Hydrochloride | 240.00 | 52.40 |
| Xanthan Gum (Keltrol TF) | 80.00 | 17.46 |
| Sodium alginate (Keltone LVCR) | 40.00 | 8.73 |
| Cross-linked polyvinylpyrrolidone (Kollidon CL-M) | 40.00 | 10.92 |
| Sodium bicarbonate | 50.00 | 8.73 |
| Magnesium Stearate | 4.00 | 0.87 |
| Talc | 4.00 | 0.87 |
| Total | 458.00 | 100% |

Tablets were prepared and tested for dissolution as described in Example 1. The dissolution results are given in Table 14.

TABLE 14

| Time (hrs) | Cumulative Percent Release |
|---|---|
| 1 | 26.80 |
| 2 | 33.28 |
| 4 | 45.00 |
| 6 | 54.60 |
| 8 | 62.58 |
| 10 | 70.38 |
| 12 | 76.80 |

EXAMPLE 8

This example illustrates the present invention when the active ingredient is ranitidine hydrochloride. The pharmaceutical composition is given in Table 15.

TABLE 15

| Ingredient | Weight (mg/tablet) | % w/w |
|---|---|---|
| Ranitidine Hydrochloride | 300.00 | 66.67 |
| Xanthan Gum (Keltrol TF) | 20.00 | 4.44 |
| Sodium alginate (Keltone LVCR) | 20.00 | 4.44 |
| Cross-linked carboxymethylcellulose | 50.00 | 11.11 |
| Sodium bicarbonate | 50.00 | 11.11 |
| Magnesium Stearate | 5.00 | 1.11 |
| Talc | 5.00 | 1.11 |
| Total | 450.00 | 100% |

Tablets were prepared and tested for dissolution as described in Example 1. The dissolution results are given in Table 16.

TABLE 16

| Time (hrs) | Cumulative Percent Release |
|---|---|
| 1 | 34.97 |
| 2 | 48.37 |
| 4 | 65.27 |
| 6 | 75.87 |
| 8 | 84.37 |

EXAMPLE 9

This example illustrates the present invention when the active ingredient is Captopril. The pharmaceutical composition is given in Table 17.

TABLE 17

| Ingredient | Weight (mg/tablet) | % w/w |
|---|---|---|
| Captopril | 100.00 | 37.88 |
| Xanthan Gum (Keltrol TF) | 50.00 | 18.94 |
| Sodium alginate (Keltrol LVCR) | 25.00 | 9.47 |
| Avicel PH 102 | 24.00 | 9.10 |
| Sodium starch gycolate (Primogel) | 30.00 | 11.37 |
| Sodium bicarbonate | 30.00 | 11.37 |
| Magnesium Stearate | 3.00 | 1.14 |
| Talc | 2.00 | 0.76 |
| Total | 264.00 | 100% |

Tablets were prepared and tested for dissolution as described in Example 1. The dissolution results are given in Table 18.

TABLE 18

| Time (hrs) | Cumulative Percent Release |
|---|---|
| 1 | 35.15 |
| 2 | 57.33 |
| 4 | 82.72 |
| 6 | 98.03 |

EXAMPLE 10

Gastric Retention Studies

This example demonstrates that the Controlled Gas Powered System prepared according to the present invention is retained for longer periods than hydrophilic matrix tablets, floating capsules and bioadhesive tablets.

The bioadhesive tablet was prepared as a bilayer tablet. The drug layer composition is given in Table 19, and the bioadhesive layer composition is given in Table 20.

TABLE 19

| Ingredient | Weight (mg/tablet) |
|---|---|
| Ciprofloxacin hydrochloride monohydrate | 599.99 |
| Hydroxypropylcellulose-L | 20.00 |
| Disodium hydrogen phosphate | 25.00 |
| Citric Acid | 25.00 |
| Talc | 7.00 |
| Magnesium Stearate | 15.00 |
| Aerosil 200 | 10.00 |
| Total | 701.99 |

TABLE 20

| Ingredient | Weight (mg/tablet) |
|---|---|
| Hydroxypropyl methylcellulose (Methocel K4M) | 215.00 |
| Cross-linked polyacrylic acid (Carbopol 934 P) | 75.00 |
| Dicalcium phosphate | 145.00 |
| Sodium benzoate | 8.00 |
| Talc | 2.00 |
| Aerosil-200 | 2.50 |
| Sunset Yellow | 2.50 |
| Total | 450.00 |

The tablets were prepared by conventional steps of mixing, roll compaction, sieving, blending with the lubricants and compression into bi-layered tablets. 70 mg of barium sulphate was incorporated into the bioadhesive layer to function as x-ray contrast medium. Gastric retention studies of the bioadhesive bi-layered tablets were done on healthy male volunteers who were given two tablets following a standard breakfast. X-ray images were recorded periodically. The bioadhesive tablets were retained in the stomach for 2.5 to 3.5 hrs.

Hydrophilic matrix tablets with the composition given in Table 21 were also prepared.

TABLE 21

| Ingredient | Weight (mg/tablet) |
| --- | --- |
| Ciprofloxacin hydrochloride monohydrate | 599.99 |
| Hydroxypropyl methylcellulose (Methocel K4M) | 20.00 |
| Hydroxypropylcellulose-L | 40.00 |
| Citric Acid | 25.00 |
| Disodium hydrogen phosphate | 25.00 |
| Talc | 10.00 |
| Magnesium Stearate | 10.00 |
| Total | 729.99 |

70 mg of barium sulfate was also incorporated into the above composition. The tablets were prepared by conventional steps of mixing, roll compaction, sieving, blending with the lubricants and compression into tablets.

Floating capsules with the composition given in Table 22 were also prepared.

TABLE 22

| Ingredient | Weight (mg/capsule) |
| --- | --- |
| Ciprofloxacin hydrochloride monohydrate | 599.99 |
| Hydroxypropyl methylcellulose (Methocel K4M) | 30.00 |
| Hydroxypropylcellulose-L | 30.00 |
| Citric Acid | 5.00 |
| Disodium hydrogen phosphate | 5.00 |
| Talc | 4.00 |
| Magnesium Stearate | 6.00 |
| Total | 679.99 |

50 mg of barium sulphate was incorporated into the above composition. Gastric retention studies were done on healthy male volunteers who were given two tablets/capsules after a standard breakfast. X-ray images were recorded periodically. The hydrophilic matrix tablets were retained for 2 to 2.5 hrs, and the floating capsules for 3.5 to 4.5 hrs. Gastric retention studies were also done on the Controlled Gas Powered System having the composition given in Example 1. The volunteers were given two tablets after a standard breakfast. Magnetic resonance imaging confirmed that the tablets according to the present invention were retained in the stomach for a period of 5 to 7 hrs.

In another experiment, a randomized, three-treatment, three period, cross-over pilot bioavailability study was conducted for formulation A (two ciprofloxacin hydrochloride 500 mg tablets, for once-daily administration, prepared according to Example 1), formulation B (ciprofloxacin free base 1000 mg tablets, for once-daily administration, prepared according to Example 2), and reference formulation R (Cipro™ (Bayer Corp.) 500 mg immediate release tablets given twice daily). The tablets were administered 30 minutes after a standard breakfast. The mean serum concentration-time profile is given in FIG. 1. Both the once-daily formulations (A and B) gave an extent of absorption comparable to the immediate release tablets (R). Thus, it can be inferred that the time period of release of drug into gastric fluid was adjusted such that it was about the same as or less than the retention time of the tablets at the site of absorption. Furthermore, formulation B gave a serum concentration time profile that would be desirable for a once-daily formulation in that the peak serum concentration was comparable to that for the immediate release drug, and the effective serum concentrations of the drug were maintained for longer periods.

EXAMPLE 11

In some respects, formulation B of the prior Example did not give as good results as the twice-daily Cipro™ 500 mg tablets. For example, the Area Under the Curve above the Minimum Inhibitory Concentration (AUC above MIC) for formulation B was less than that of conventional Cipro™ tablets.

An improved once-daily 1,000 mg ciprofloxacin free base formulation (the "OD" formulation) was developed, the composition of which is given in Table 23. In the OD formulation, the amount of gel forming polymer (sodium alginate) is about one-half that of formulation B (0.49% vs. 1.0%).

TABLE 23

| Ingredients | Weight (mg/tablet) | % w/w of the tablet |
| --- | --- | --- |
| Ciprofloxacin base | 1000.0 | 69.9 |
| Sodium alginate | 5.0 | 0.34 |
| Xanthan gum | 15.0 | 1.03 |
| Sodium bicarbonate | 200.0 | 13.74 |
| Cross-Linked polyvinyl pyrrolidone (Kollidon CL-M) | 176.8 | 12.15 |
| Magnesium stearate | 33.0 | 2.26 |
| Talc | 10.0 | 0.68 |
| Total | 1440 | 100 |

Tablets were prepared from the components in Table 23 and tested for dissolution as described earlier. Remarkably, it was observed that the in vitro dissolution profile of the OD formulation (Table 24) was much faster releasing than formulation B. Thus, more than 80% of the drug in the OD tablets were released within 4 hours as compared to 8 hours for formulation B. Compare Table 23 with Table 24.

TABLE 24

| Time (hrs. | Cumulative percent Release |
| --- | --- |
| 1 | 35.49 |
| 2 | 53.61 |
| 4 | 82.33 |
| 6 | 98.72 |

The mean stomach retention of the OD tablets was studied by magnetic resonance imaging and was found to be 5.33 hours which correlated well with the 6 hour dissolution profile of these tablets.

In order to compare the pharmacokinetic and pharmacodynamic parameters of this once daily formulation, a randomized, three period, balanced crossover bioavailability study was conducted in 12 healthy, adult male human subjects, between 18–45 years of age where one dose of ciprofloxacin 1000 mg OD tablets was administered 30 minues after a standard high fat breakfast. The immediate release Cipro™ tablets were tested under both fed and fasted conditions.

Under fed conditions, two oral doses of 500 mg immediate release Cipro™ tablets were given. The first oral dose was given within 30 mins. of a high fat breakfast and the second dose was given 12 hours later after a high fat meal (dinner).

Under fasted conditions, two oral doses of 500 mg tablets of the Cipro™ immediate release tablets were administered. The first oral dose was given after an overnight fast, and the second oral dose was given 12 hours later but four hours after a light meal.

Figure 2:
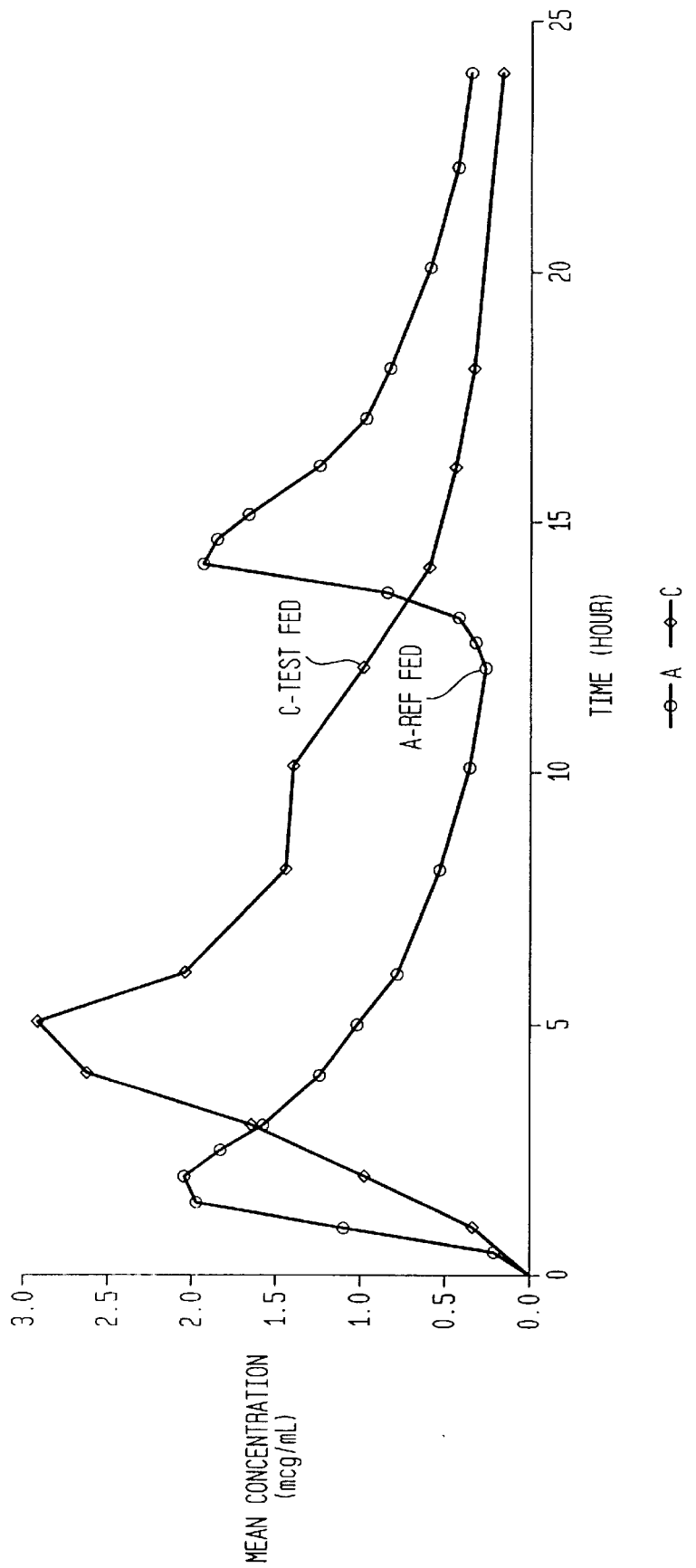
FIGS. 2 and 3 are graphs illustrating mean serum concentration vs. time for ciprofloxacin free base when incorporated in the oral controlled drug delivery system according to Table 23 below as compared to Cipro™ immediate release tablets under fed and fasting conditions.
Figure 3:
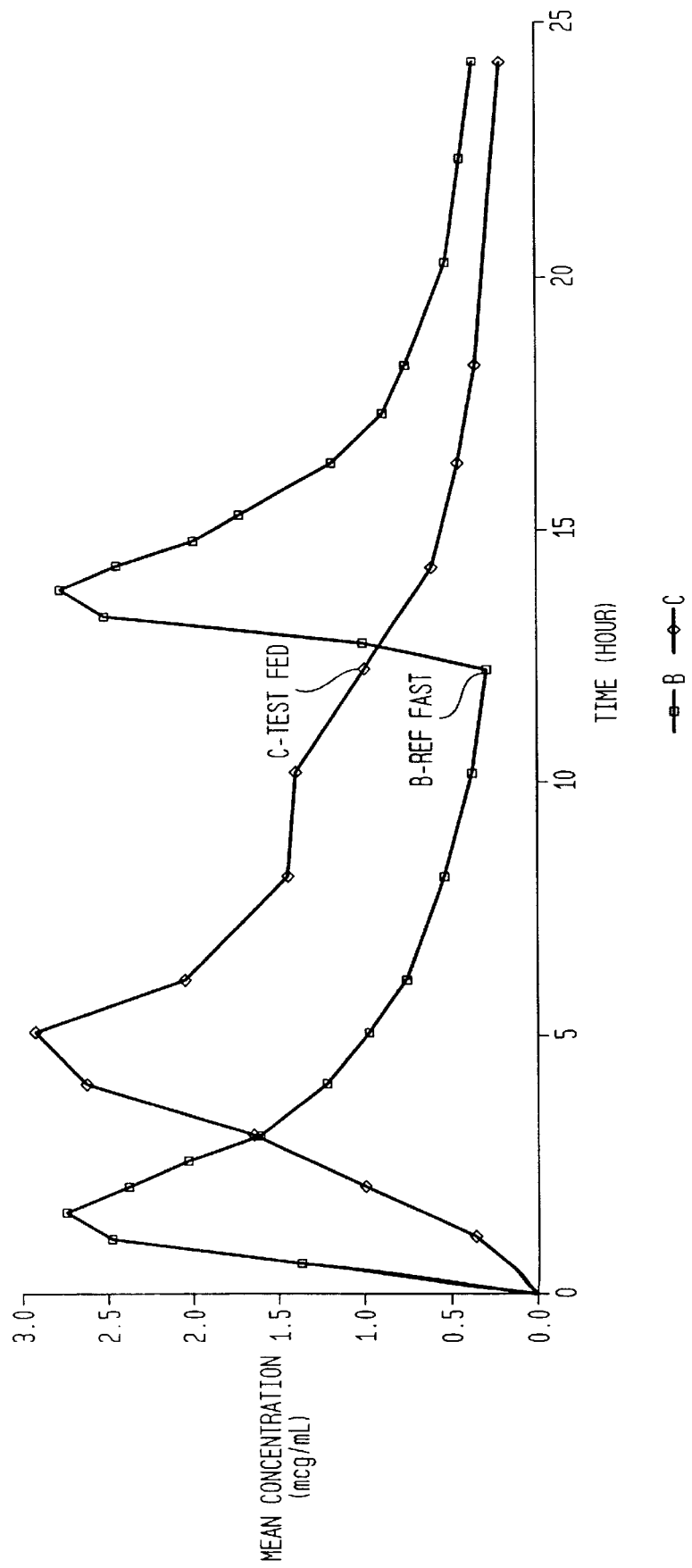

The results of the study are shown in FIGS. 2 and 3, where FIG. 2 shows the serum concentration over time of the OD tablets (fed) vs. Cipro™ (fed), and FIG. 3 shows the serum concentration of the OD tablets (fed) vs. Cipro™ (fasted).

The OD formulation gave a serum concentration time profile desirable for once daily dosage form in that the peak serum concentration (Cmax) was comparable to that for the immediate release drug indicating a similar rate of absorption of the drug. The total bioavailability of the drug $AUC_{(O-\alpha)}$ (Area Under the Curve) was also comparable to that of immediate release tablets indicating that all of the drug is released from the formulation during its residence time in the stomach. See Table 25.

TABLE 25

| Study | Cmax (μg/ml) | $AUC_{(0-\alpha)}$ (μg · h/ml) |
|---|---|---|
| Ciprofloxacin 1000 mg. OD (Fed) | 3.04 | 24.81 |
| Cipro ™ 500 mg Bid (Fasted) | 3.17 | 26.28 |
| Cipro ™ 500 Mg Bid (Fed) | 2.66 | 22.39 |

Table 26 gives the AUC above MIC at the three levels of 0.1 μg/ml, 0.25 μg/ml and 0.5 μg/ml for ciprofloxacin OD 1000 mg vs. Cipro™ 500 mg bid. These values for ciprofloxacin OD were better than those for Cipro™ immediate release tablets administered twice daily under fed conditions, indicating better therapeutic efficacy of the OD formulation when both immediate and controlled dosage forms were administered after food. The therapeutic efficacy of the OD tablets under fed condition was comparable to the therapeutic efficacy of the Cipro™ immediate release tablets administered under fasting conditions.

TABLE 26

| | AUC above MIC | | |
|---|---|---|---|
| Treatment | 0.1 μg/ml · h | 0.25 μg/ml · h | 0.5 μg/ml · h |
| Ciprofloxacin base 1000 mg, OD (Fed) | 20.7 ± 4.4 | 17.4 ± 4.3 | 13.2 ± 4.1 |
| Cipro ™ 2 × 500 mg bid (Fasted) | 21.5 ± 3.7 | 18.0 ± 3.8 | 13.4 ± 4.0 |
| Cipro ™ 2 × 500 mg bid (Fed) | 17.68 ± 3.9 | 14.2 ± 3.9 | 9.7 ± 3.4 |

Thus, a minor change in the percentage of hydrophilic polymer (sodium alginate) from 0.71% w/w of the composition to 0.34% w/w of the composition resulted in a dramatic and unexpected improvement in the pharmacodynamic and pharmacokinetic parameters, which are important measures of therapeutic efficacy.

While the invention has been described by reference to specific examples, this was for purposes of illustration only. Numerous alternative embodiments will be apparent to those skilled in the art and are considered to be within the scope of the invention.

What is claimed is:

1. A once daily tablet formulation for oral administration in humans for the controlled release of ciprofloxacin comprising a pharmaceutically effective amount of ciprofloxacin, about 0.2% to about 0.5% sodium alginate, about 0.5 to about 2.0% xanthan gum, about 10.0% to about 25% sodium bicarbonate, and about 5.0% to about 20% cross-linked polyvinylpyrrolidone, said percentages being w/w of the composition, wherein the weight ratio of sodium alginate to xanthan gum is between about 1:1 to about 1:10.

2. The formulation of claim 1 comprising 69.9% ciprofloxacin base, 0.34% sodium alginate, 1.03% xanthan gum, 13.7% sodium bicarbonate, 12.1% cross-linked polyvinylpyrrolidone, and optionally other pharmaceutical excipients.

3. The formulation of claim 1 in the form of a tablet.

4. A once daily homogenous, single layer tablet formulation for oral administration in humans for the controlled release of ciprofloxacin in the stomach or upper part of the small intestine comprising a pharmaceutically effective amount of ciprofloxacin, about 0.2% to about 0.5% sodium alginate, about 0.5 to about 2.0% xanthan gum, about 10.0% to about 25% sodium bicarbonate, and about 5.0% to about 20% cross-linked polyvinylpyrrolidone, said percentages being w/w of the composition, wherein the weight ratio of sodium alginate to xanthan gum is between about 1:1 to about 1:10.

5. The formulation of claim 4 comprising 69.9% ciprofloxacin base, 0.34% sodium alginate, 1.03% xanthan gum, 13.7% sodium bicarbonate, 12.1% cross-linked polyvinylpyrrolidone, and optionally other pharmaceutical excipients.

6. A once daily tablet formulation for oral administration in humans for the controlled release of ciprofloxacin in the stomach or upper part of the small intestine comprising a pharmaceutically effective amount of ciprofloxacin, about 0.2% to about 0.5% sodium alginate, about 0.5 to about 2.0% xanthan gum, about 10.0% to about 25% sodium bicarbonate, and about 5.0% to about 20% cross-linked polyvinylpyrrolidone, said percentages being w/w of the composition, wherein the weight ratio of sodium alginate to xanthan gum is between about 1:1 to about 1:10, said ingredients present in said relative proportions in a single layer.

7. The formulation of claim 6 comprising 69.9% ciprofloxacin base, 0.34% sodium alginate, 1.03% xanthan gum, 13.7% sodium bicarbonate, 12.1% cross-linked polyvinylpyrrolidone, and optionally other pharmaceutical excipients.

8. The formulation of claim 6 in the form of a tablet.

9. A once daily tablet formulation for oral administration in humans for the controlled release of ciprofloxacin in the stomach or upper part of the small intestine comprising a pharmaceutically effective amount of ciprofloxacin, about 0.2% to about 0.5% sodium alginate, about 0.5 to about 2.0% xanthan gum, about 10.0% to about 25% sodium bicarbonate, and about 5.0% to about 20% cross-linked polyvinylpyrrolidone, said percentages being w/w of the composition, wherein the weight ratio of sodium alginate to xanthan gum is between about 1:1 to about 1:10.

10. The formulation of claim 9 comprising 69.9% ciprofloxacin base, 0.34% sodium alginate, 1.03% xanthan gum, 13.7% sodium bicarbonate, 12.1% cross-linked polyvinylpyrrolidone, and optionally other pharmaceutical excipients.

11. The formulation of claim 9 in the form of a tablet.

* * * * *